US010357227B2

(12) United States Patent
Sinkus et al.

(10) Patent No.: US 10,357,227 B2
(45) Date of Patent: Jul. 23, 2019

(54) DETERMINATION OF THE CONCENTRATION DISTRIBUTION OF SONICALLY DISPERSIVE ELEMENTS

(71) Applicant: KONINKLIJKE PHILIPS N.V., Eindhoven (NL)

(72) Inventors: Ralph Roman Sinkus, Eindhoven (NL); Simon Auguste Lambert, Eindhoven (NL); Leon Christiaan Ter Beek, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 317 days.

(21) Appl. No.: 14/770,275

(22) PCT Filed: Feb. 11, 2014

(86) PCT No.: PCT/IB2014/058892
§ 371 (c)(1),
(2) Date: Aug. 25, 2015

(87) PCT Pub. No.: WO2014/128593
PCT Pub. Date: Aug. 28, 2014

(65) Prior Publication Data
US 2016/0007968 A1     Jan. 14, 2016

(30) Foreign Application Priority Data

Feb. 25, 2013    (EP) .................................... 13305209

(51) Int. Cl.
*A61B 5/00*      (2006.01)
*A61B 8/00*      (2006.01)
(Continued)

(52) U.S. Cl.
CPC ............ *A61B 8/485* (2013.01); *A61B 5/0051* (2013.01); *A61B 5/055* (2013.01); *A61B 8/08* (2013.01);
(Continued)

(58) Field of Classification Search
CPC . A61B 5/00; A61B 8/00; G01R 33/00; G01N 29/00
See application file for complete search history.

(56) References Cited

U.S. PATENT DOCUMENTS 2,839,915 A     6/1958    Roth et al.
4,881,549 A *   11/1989   Rhyne ...................... A61B 8/08
                                                                              600/443
(Continued)

FOREIGN PATENT DOCUMENTS

| CN | 101708123 A | 5/2010 |
| CN | 101912278 A | 12/2010 |
| WO | 0070362 | 11/2000 |

OTHER PUBLICATIONS

Madsen, Ernest L., H. John Sathoff, and James A. Zagzebski. "Ultrasonic shear wave properties of soft tissues and tissuelike materials." The Journal of the Acoustical Society of America 74.5 (1983): 1346-1355.*
(Continued)

*Primary Examiner* — Luther Behringer
*Assistant Examiner* — Sean D Mattson

(57) ABSTRACT

A medical apparatus (200, 300, 400, 500) determines the concentration distribution of sonically dispersive elements (606, 2001) within a subject (306, 604, 1004), wherein the medical apparatus comprises: a memory (212) for storing machine executable instructions (224, 226, 228, 230, 232, 318) and a processor (206) for executing the machine executable instructions. Execution of the instructions cause the processor to: receive (100) shear wave data (214)
(Continued)

descriptive of the propagation of shear waves (310, 608, 1118) within the subject for at least two frequencies; determine (102) a mechanical property (316, 618, 620) of the subject using the shear wave data at each of the at least two frequencies; determine (104) a power law relationship (218, 702) between the at least two frequencies and the mechanical property; and determine (106) the concentration distribution of the sonically dispersive elements within the subject using the power law relationship and calibration data (222, 704, 800).

19 Claims, 12 Drawing Sheets

(51) Int. Cl.
  *A61B 8/08* (2006.01)
  *A61B 5/055* (2006.01)
  *G01R 33/563* (2006.01)

(52) U.S. Cl.
  CPC .............. *A61B 8/58* (2013.01); *A61B 8/585* (2013.01); *G01R 33/56358* (2013.01); *A61B 8/0891* (2013.01)

(56) References Cited

U.S. PATENT DOCUMENTS

| | | | |
|---|---|---|---|
| 6,059,727 A * | 5/2000 | Fowlkes | A61B 8/08 128/916 |
| 8,347,692 B2 | 1/2013 | Sinkus et al. | |
| 9,351,707 B2 | 5/2016 | Tamura | |
| 2004/0210120 A1 | 10/2004 | Wang et al. | |
| 2008/0066551 A1* | 3/2008 | Panetta | G01N 29/032 73/584 |
| 2010/0138163 A1 | 6/2010 | Gallippi et al. | |
| 2010/0160778 A1* | 6/2010 | Eskandari | A61B 8/00 600/438 |
| 2010/0170342 A1* | 7/2010 | Sinkus | A61B 8/08 73/597 |
| 2011/0092817 A1* | 4/2011 | Cloutier | A61B 8/06 600/437 |
| 2012/0111117 A1* | 5/2012 | Prakash | G01N 29/032 73/599 |
| 2012/0302883 A1* | 11/2012 | Kong | A61N 7/02 600/439 |
| 2013/0031981 A1* | 2/2013 | Montaldo | G01S 7/52036 73/606 |
| 2014/0016438 A1* | 1/2014 | Franceschini | G01S 15/02 367/87 |

OTHER PUBLICATIONS

Szabo, Thomas L. "Causal theories and data for acoustic attenuation obeying a frequency power law." The Journal of the Acoustical Society of America 97.1 (1995): 14-24.*

Kytömaa, Harri K. "Theory of sound propagation in suspensions: a guide to particle size and concentration characterization." Powder Technology 82.1 (1995): 115-121.*

Schiessel, H., et al. "Generalized viscoelastic models: their fractional equations with solutions." Journal of physics A: Mathematical and General 28.23 (1995): 6567.*

Sinkus et al "Viscoelastic Shear Properties of In Vivo Breast Lesions Measured by MR Elastography" Magnetic Resonance Imaging 23 (2005) p. 159-165.

Mariappan et al, "Magnetic Resonance Elastography: A Review" Clinical Anatomy 23 p. 497-511 (2010).

Guo et al "Fractal Network Dimension and Viscoelastic Powerlaw Behavior II: An Experimetal Study of Structure-Mimiking.." Physics in Medicine and Biology, 57 (2012) p. 4041-4053.

Posnansky et al "Fractal Network Dimension and Viscoelastic Powerlaw Behavior I: A Modelign Approach Based on a Coarse-Graining.." Physics in Medicine and Biology, 57 (2012) p. 4023-4040.

Coussot et al "Fractional Derivative Models for Ultrasonic Characterization of Polymer and Breast Tissue Viscoelasticity" IEEE Trans. on Ultrasonics, Ferroelectrics and Frequency Control, vol. 56, No. 5, Apr. 2009 p. 715-725.

Rump et al "Fractional Encoding of Harmonic Motions in MR Elastography" Magnetic Resonance in Med. 57: p. 388-395 (2007).

* cited by examiner

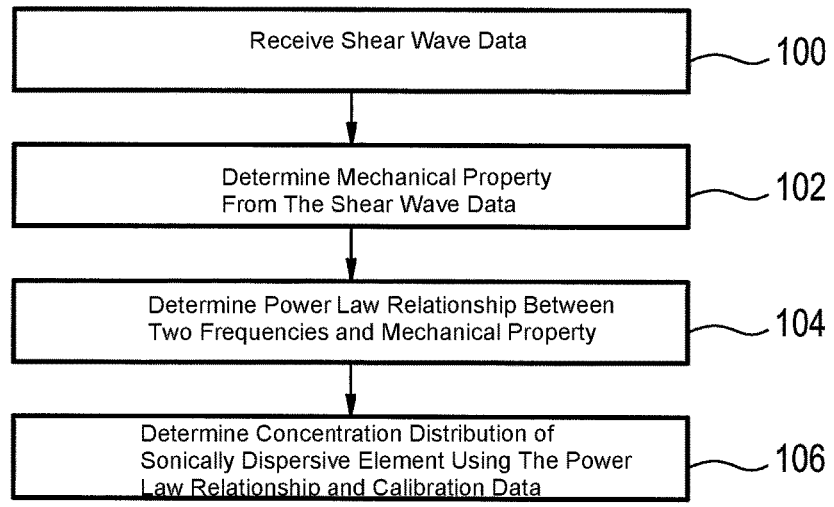
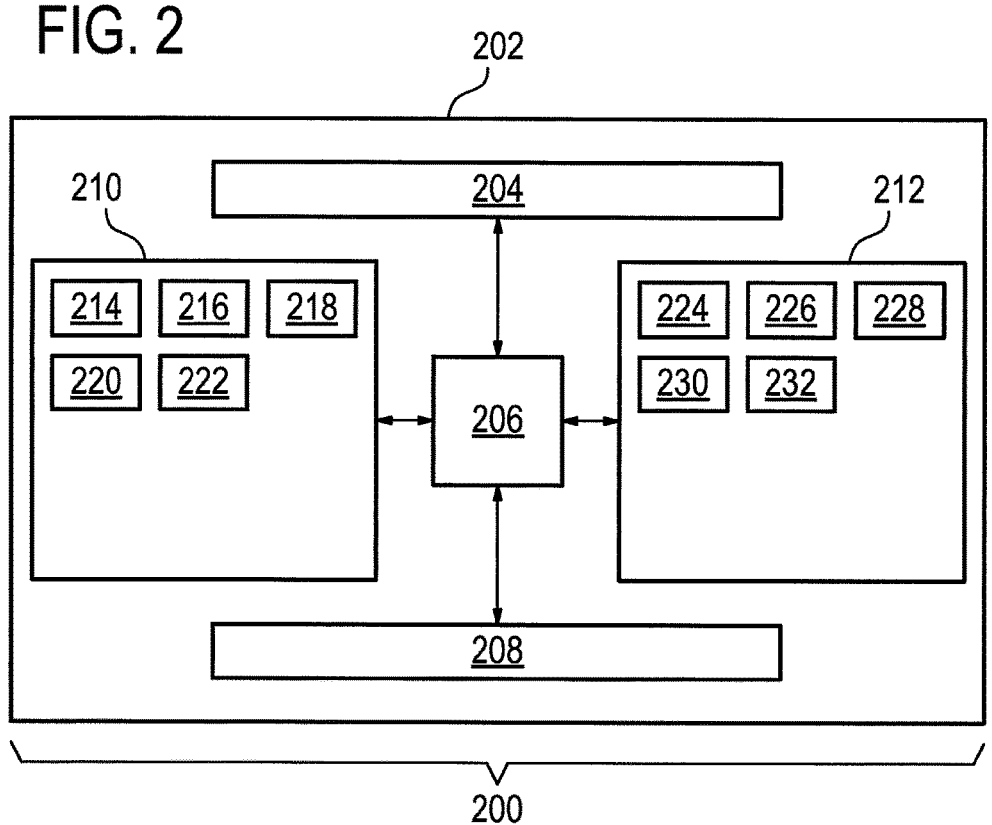

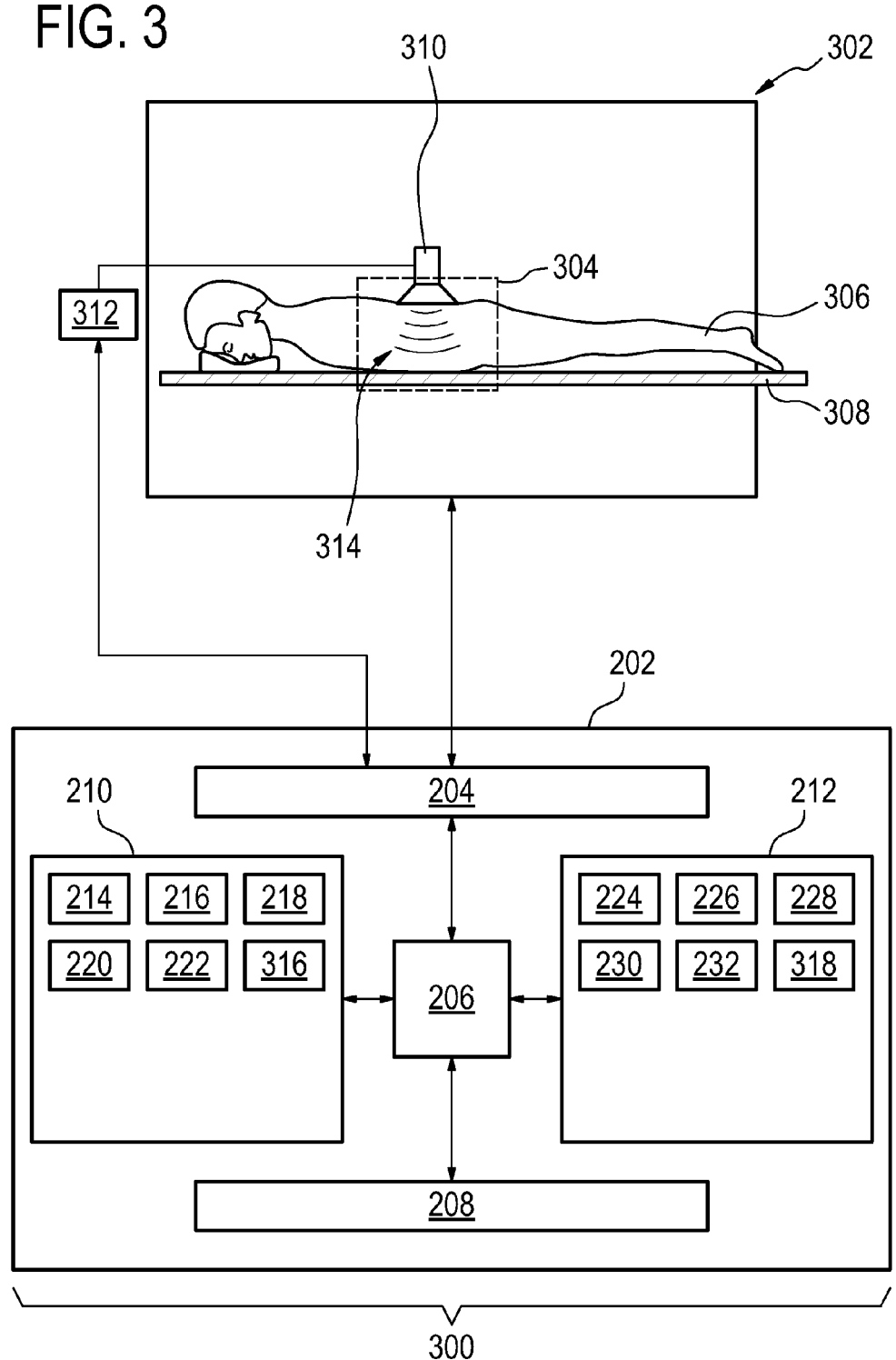

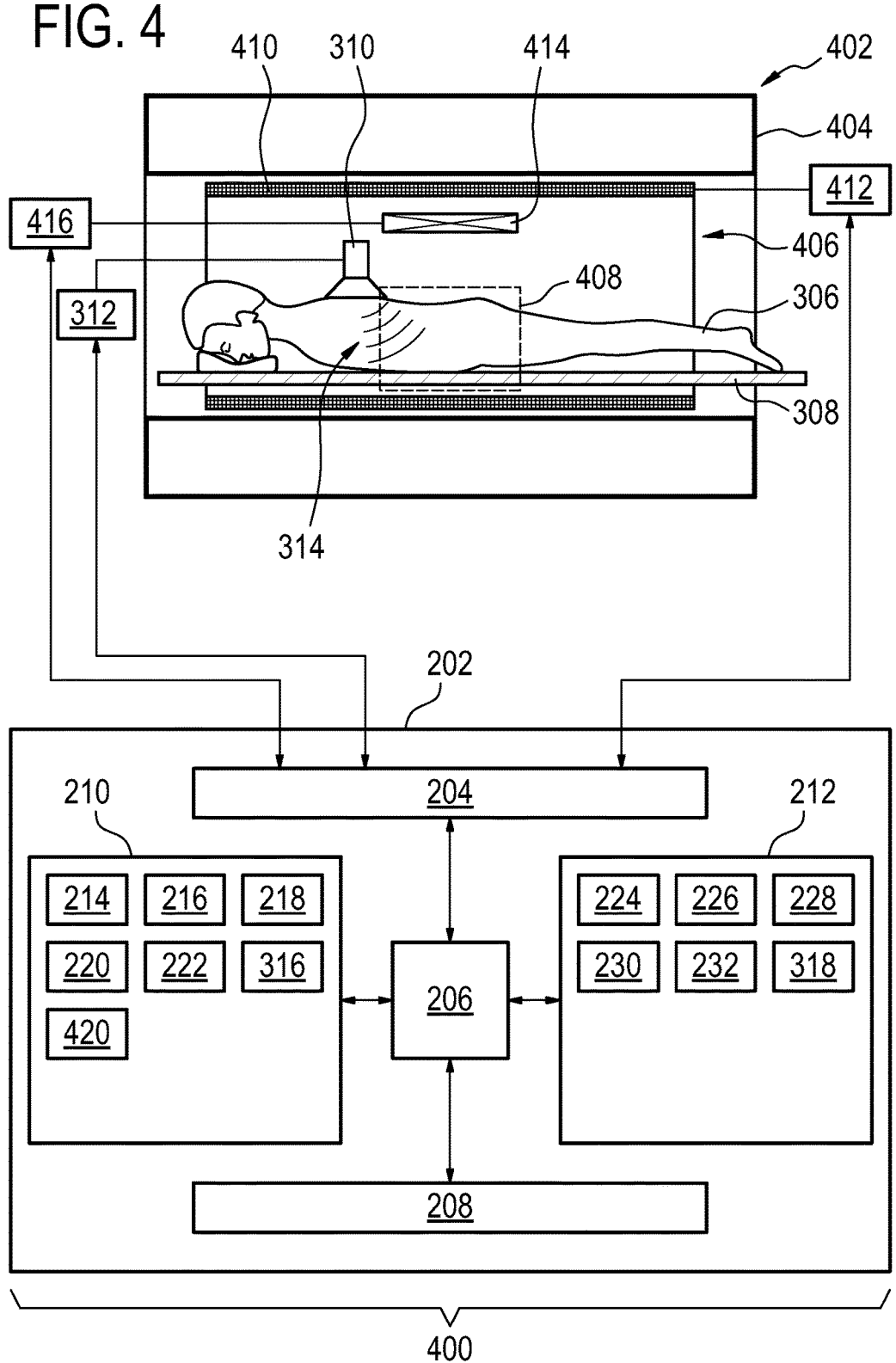

DETERMINATION OF THE CONCENTRATION DISTRIBUTION OF SONICALLY DISPERSIVE ELEMENTS

CROSS-REFERENCE TO PRIOR APPLICATIONS

This application is the U.S. National Phase application under 35 U.S.C. § 371 of International Application No. PCT/IB2014/058892, filed on Feb. 11, 2014, which claims the benefit of EP Patent Application No. EP13305209.2, filed on Feb. 25, 2013. These applications are hereby incorporated by reference herein.

TECHNICAL FIELD

The invention relates to the determination of the distribution of sonically dispersive elements within a subject, in particular to the determination of this distribution using medical imaging.

BACKGROUND OF THE INVENTION

It may the technologically or medically beneficial to know understand microstructure of an object or tissue. For instance knowing the number of particles or blood vessels within a particular volume or cross section may impart information descriptive of the structure or even be useful in assisting in diagnosis of a pathology.

In PCT patent application WO 00/70362 Magnetic Resonance Elastography is used to measure Young's modulus at a single frequency using longitudinal waves.

In Sinkus et. al. "Viscoelastic shear properties of in vivo breast lesions measured by MR elastography," Magnetic Resonance Imaging 23 (2005) 159-165 a technique for measuring the shear viscosity and shear modulus using magnetic resonance imaging.

Magnetic Resonance Elastography is reviewed in the journal article Mariappan et. al., "Magnetic Resonance Elastography: A Review," Clin. Anat. 2010 July; 23(5) 497-511; doi:10.1002/ca.21006.

SUMMARY OF THE INVENTION

The invention provides for a medical apparatus, a computer program product and a method in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

Medical image data is defined herein as two or three dimensional data that has been acquired using a medical imaging scanner. A medical imaging scanner is defined herein as a apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Magnetic Resonance Elastography data is Magnetic Resonance data that has been acquired in the course of performing magnetic resonance elastography.

In one aspect the invention provides for a medical apparatus for determining the concentration distribution of sonically dispersive elements within a subject. A sonically dispersive element as used herein encompasses a particle or structure within the subject which has an acoustic impedance that is sufficiently different from the surrounding medium that it causes the dispersion of acoustic waves.

The medical apparatus comprises a memory for storing machine-executable instructions and a processor for executing the machine-executable instructions. Execution of the instructions causes the processor to receive shear wave data descriptive of the propagation of shear waves within the subject for at least two frequencies. The shear wave data may take different forms but it is at least descriptive of the propagation of the shear waves in time and at least two different propagation frequencies or generation frequencies for the shear wave. Execution of the instructions further causes the processor to determine a mechanical property of the subject using the shear wave data at each of the at least two frequencies. The mechanical property used herein is a mechanical property which can be derived from the propagation of the shear waves. The mechanical property may have a spatial dependence. The shear wave data may also be spatially descriptive also.

Execution of the instructions further causes the processor to determine a power law relationship between the at least two frequencies and the mechanical property. A power law relationship as used herein is the conventional mathematical usage. Essentially the mechanical property has a dependency on the frequency raised to a power. Execution of the instructions further causes the processor to determine the concentration distribution of the sonically dispersive elements within the subject using the power law relationship and calibration data. This embodiment may be beneficial because the microstructure or essentially the concentration of the sonically dispersive elements within the subject can be determined solely by the propagation of the shear waves within the subject. Information about the concentration of a single type of dispersive element can be determined as well as information about dispersive elements which have a distribution of sizes. This could include mixtures of different types of dispersive elements also. The microstructure may be characterized in terms of a grain size distribution, which would be descriptive of the concentration of several sizes of dispersive elements.

This may have various uses such as detecting the concentration of particles within a matrix or even may have medical applications such as detecting the density of blood vessels or other objects within a subject. It could also be useful for inferring information about the nature of the dispersive elements. For instance the size and density of blood vessels may follow a particular distribution within a subject. Knowing this information may be useful for diagnostic or research purposes.

The calibration data may take different forms, for instance the calibration data may be determined by taking empirical measurements on subjects within known concentrations or it may also be determined theoretically studying the scattering or modeling the scattering of the shear waves from the sonically dispersive elements.

In another embodiment the medical apparatus further comprises a medical imaging system for measuring the shear wave data. Execution of the machine-executable instructions causes the processor to acquire the shear wave data using the medical imaging system. The medical imaging system as used herein is any imaging system which is able to non-invasively detect the traveling of shear waves within the subject. Examples would include an ultrasound system and a magnetic resonance imaging system.

In another embodiment the medical imaging system is an ultrasound system. The ultrasound system is operable to acquire ultrasound data. The ultrasound system is operable to determine the shear wave by tracking speckle patterns in the ultrasound data. Speckle pattern is an intensity pattern in the ultrasound image which is produced by mutual interferences from a variety of wave fronts. As such the speckle pattern is dependent upon the internal structure of the subject. As the subject moves internally due to a shear wave the speckle patterns in the image will move. This tracking the position of the speckle patterns allows the determination of the internal movement of the subject. This can be used to create a mapping of the traveling of the shear wave fronts through the subject. In this way the shear wave data can be derived directly from the ultrasound data. This embodiment may be beneficial because ultrasound is non-invasive and enables the measurement of the shear wave data without any damage to the subject.

In another embodiment the medical imaging system is a magnetic resonance imaging system. The magnetic resonance imaging system is operable to acquire magnetic resonance elastography data. The magnetic resonance imaging system is operable to determine the shear wave data using the magnetic resonance elastography data. Magnetic resonance elasotraphy is explained in detail in the journal article Rump et. al., "Fractional Encoding of Harmonic Modtions in MR Elastography," Magnetic Resonance in Medicine, 57: 388-395 (2007). The fractional MRE techniques described in this article are applicable to the present invention.

This embodiment may be beneficial because magnetic resonance imaging is able to measure the harmonic motion of the internal structure of the subject very accurately. This will enable the measurement of the shear wave propagation in different portions of the subject as a function of time.

In another embodiment the medical apparatus further comprises a vibration system operable for inducing shear waves in the subject. Execution of the machine-executable instructions further cause the processor to cause shear waves in the subject using the vibration system. The shear wave data is descriptive of the shear waves created by the vibration system. This embodiment is particularly advantageous because the medical apparatus is able to generate shear waves in the subject and acquire the shear wave data automatically.

In another embodiment the vibration system is an ultrasound transducer or a mechanical actuator.

In another embodiment the vibration system is a high-intensity focused ultrasound system. The high-intensity focused ultrasound system is operable for inducing the shear waves using sonic radiation force. The frequency at which high-intensity focused ultrasound systems operate may be too high to be used to generate shear waves directly. However, the ultrasound focused at the focal point of the high-intensity focused ultrasound system may be pulsed or modulated. This pulsing or modulating generates a sonic radiation force which varies in times. This embodiment may be particularly beneficial because the shear waves can be selectively generated originating at a particular point within the subject. This may be particularly useful if a certain portion of the subject wants to be studied internally.

In another embodiment the vibration system is operable to generate shear waves with a frequency between 10 Hz to 1000 Hz. This embodiment may be particularly valuable because this is a frequency at which shear waves may be generated at within tissue.

In another embodiment the shear wave data, the mechanical property, the power law relationship, and the concentration distribution of the sonically dispersive elements have a two-dimensional spatial dependence or a three-dimensional spatial dependence. This embodiment may be advantageous because it may be beneficial to know the two or three-dimensional distribution of the sonically dispersive elements within the subject.

In another embodiment execution of the machine-executable instructions further cause the processor to perform any one of the following: store the concentration distribution of the sonically dispersive elements in the memory, display the concentration distribution of the sonically dispersive elements on a display, send the concentration distribution of the sonically dispersive elements to a computer system via a computer network, and combinations thereof.

In some embodiments the concentration distribution of the sonically dispersive element may be displayed with other graphical information such as a medical image or images acquired using the magnetic resonance imaging system or a diagnostic ultrasound system.

In another embodiment execution of the machine-executable instructions further cause the processor to generate the calibration data by modeling the scattering of shear waves by the sonically dispersive elements as a function of the shear wave frequency. The size of the sonically dispersive elements may also be varied in the model. In a numerical model, it is also easy to choose a distribution of sizes and/or a distribution of concentrations when performing the modeling. In this way the analysis can be extended to cases where the dispersive elements have a distribution of sizes instead.

Essentially the mechanical property can be determined as a function of frequency by modeling the system. This for instance may be achieved in a variety of different ways. For instance a finite difference model which includes dispersive elements within a surrounding matrix may be used. In another embodiment a box counting algorithm may be used to determine a fractal dimension which is used in an ordinary differential equation to predict the frequency dependence of the power law for the mechanical property.

In another embodiment the mechanical property is any one of the following: elasticity, viscosity, the propagation or propagation speed, the attenuation of the shear wave, and the dispersion relation of the shear wave.

In another aspect the invention provides for a computer program product comprising machine-executable instructions for execution by a processor controlling a medical apparatus. The medical apparatus is operable for determining the concentration distribution of sonically dispersive elements within a subject. Execution of the instructions causes the processor to receive shear wave data descriptive of the propagation of shear waves within the subject for at least two frequencies. Execution of the instructions further causes the processor to determine a mechanical property of the subject using the shear wave data at each of the at least two frequencies. Execution of the instructions further causes the processor to determine a power law relationship between the at least two frequencies and the mechanical property. Execution of the instructions further causes the processor to determine the concentration distribution of the sonically dispersive elements within the subject using the power law relationship and calibration data.

In another aspect the invention provides for a method of determining the concentration distribution of sonically dispersive elements within a subject. The method comprises the steps of receiving shear wave data descriptive of the propagation of shear waves within the subject for at least two frequencies. The method further comprises the steps of determining the mechanical property of the subject using the shear wave data at each of the at least two frequencies. The method further comprises the step of determining a power law relationship between the at least two frequencies and the mechanical property. The method further comprises the step of determining the concentration distribution of the sonically dispersive elements within the subject using the power law relationship and the calibration data.

In another embodiment the method further comprises the step of measuring the calibration power law relationship for multiple frequencies as a function of the concentration distribution of dispersive elements. So essentially at different frequencies of generating the shear waves the power law relationship can be determined empirically by using subjects or phantoms which contain different concentrations of dispersive elements or different concentration distributions of dispersive elements. The method further comprises the step of determining the calibration data empirically using the calibration power law relationship. If the concentration distribution of the dispersive elements and their size are known a priority then these measurements can be made and can be used to directly determine the calibration data empirically.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which:

FIG. 1 shows a flow chart which illustrates a method according to an embodiment of the invention.

FIG. 2 illustrates an example of a medical apparatus;

FIG. 3 illustrates a further example of a medical apparatus;

FIG. 4 illustrates a further example of a medical apparatus;

with D=2; and

Figure 17:
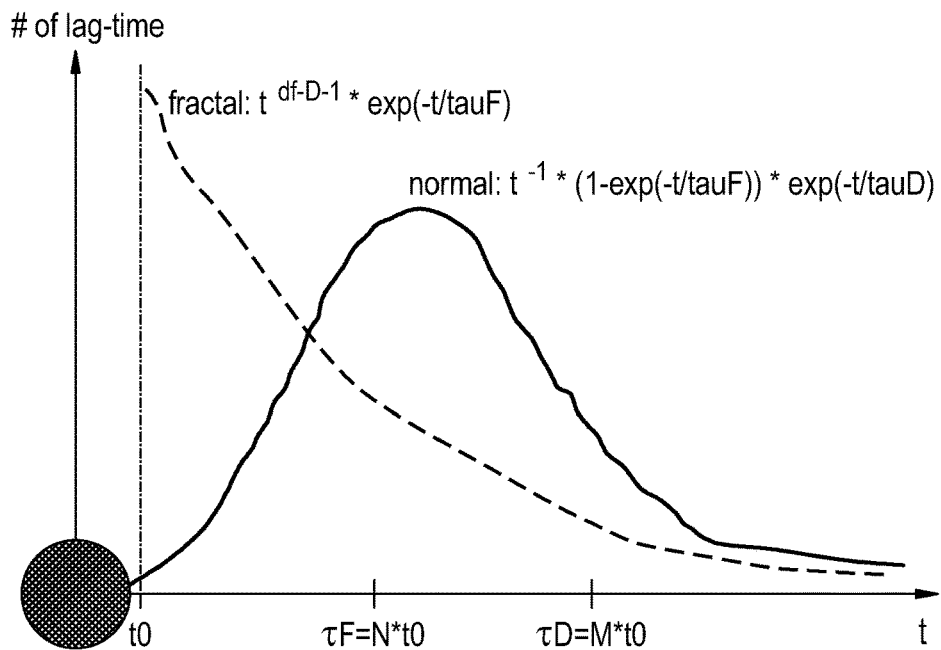

FIG. 17 shows the schematic depiction of the two contributions for the total lag-time distribution a(t).

DETAILED DESCRIPTION OF THE EMBODIMENTS

Like numbered elements in these figures are either equivalent elements or perform the same function. Elements which have been discussed previously will not necessarily be discussed in later figures if the function is equivalent.

FIG. 1 shows a flow chart which illustrates a method according to an embodiment of the invention. First in step 100 shear wave data is received which is descriptive of the propagation of shear waves within the subject for at least two frequencies. Next in step 102 a mechanical property of the subject is determined using the shear wave data at each of the at least two frequencies. Then in step 104 a power law relationship between the at least two frequencies and the mechanical property is determined. Then in step 106 the concentration distribution of the sonically dispersive element within the subject is determined using the power law relationship and calibration data. For instance a lookup table could be created which contains entries for various power law relationships values as a function of the concentration distribution of the sonically dispersive elements.

It should be noted that in some instances it may be beneficial to use a priori knowledge of the size or approximate size of the sonically dispersive elements within the subject. In some cases the size of the sonically dispersive elements may be well known. For instance if the sonically dispersive elements are blood vessels the average or typical size of blood vessels within the subject may be known beforehand and may be useful also in conjunction with the calibration data. For instance the calibration data could be for a particular type or distribution of dispersive elements.

FIG. 2 illustrates an example of a medical apparatus 200. The medical apparatus 200 comprises a computer 202. The computer 202 has a hardware interface 204 connected to a processor 206. The processor 206 is also connected to a user interface 208 and computer storage 210 and computer memory 212. Within the computer storage 210 is stored shear wave data 214. The shear wave data 214 is used to drive a mechanical property 216 which is also stored in the computer storage 210. The computer storage 210 also contains a power law relationship 218 derived or calculated from the mechanical property 216. The computer storage 210 is also shown as containing a concentration of sonically dispersive elements 220 which was calculated using the power law relationship 218 by comparing it to calibration data 222. The calibration data 222 is also shown as being stored in the computer storage 210. The shear wave data 214, the mechanical property 216, the power law relationship 218, and the concentration of the sonically dispersive elements 220 or concentration distributrion of the sonically dispersive elements may have a spatial dependence.

The computer memory 212 is shown as containing a control module 224. The control module 224 enables the processor 206 to control the operation and function of the medical apparatus 200. In the case of additional components being added to the medical apparatus 200 such as a mechanical actuator or the system for generating shear waves or a medical imaging system, the processor 206 may be enabled by the control module 224 to control them via the hardware interface 204. The computer memory 212 is further shown as containing a shear wave data processing module 226. The shear wave data processing module 226 contains computer-executable code which enables the processor 206 to determine the mechanical property 216 from the shear wave data 214.

The computer memory 212 is further shown as containing a power law determination module 228. The power law determination module 228 contains computer-executable code which enables the processor 206 to determine the power law relationship 218 from the mechanical property 216. The computer memory 212 is further shown as containing a concentration determination module 230. The concentration determination module 230 enables the processor 206 to determine the concentration of sonically dispersive elements 220 or the concentration distribution of sonically dispersive elements using the power law relationship 218 and the calibration data 222.

Finally the computer memory 212 is shown as containing a calibration data generation module 232. The calibration data generation module 232 is an optional module which in some embodiments would be used to theoretically calculate the calibration data 222. In other embodiments the calibration data generation module may use empirical measurements to derive or calculate the calibration data 222.

FIG. 3 shows a further example of a medical imaging system 300. The medical imaging system in FIG. 3 is similar to that shown in FIG. 2 except there is additionally a medical imaging system 302 and a mechanical actuator 310 are also shown as being included. The medical imaging system 302 is intended to be representative and may be any medical imaging system which is able to detect shear waves traveling through a subject 306. The medical imaging system in particular may be representative of a magnetic resonance imaging system or an ultrasound system. There is a subject 306 shown as reposing on a subject support 308 partially within an imaging zone 304.

There is a mechanical actuator 310 in contact with the subject 306 which is generating shear waves 314. In some instances there may be a catheter or object inserted into an orifice to locally generate shear waves also. The mechanical actuator 310 is connected to a mechanical actuator controller 312 which supplies electrical power or other actuation for moving the mechanical actuator 310. In the case of a magnetic resonance imaging system the mechanical actuator controller 312 may for instance provide pneumatic power to the mechanical actuator 310 or may move a non-magnetic rod. The medical imaging system 302 and the mechanical actuator controller 312 are shown as being connected to a hardware interface 204. This enables the processor 206 to control the operation and function of the various components of the medical imaging system 300.

The computer storage 210 is shown as containing medical image data 316 that was acquired using the medical imaging system 302. The computer memory 212 is shown as additionally containing an image processor module 318. The imaging processing module 318 enables the processor 206 to generate the shear wave data 214 from the medical image data 316.

FIG. 4 shows a further example of a medical apparatus 400. In this example the medical imaging system is a magnetic resonance imaging system 402. The magnetic resonance imaging system comprises a magnet 404. The magnet 404 is a cylindrical type superconducting magnet with a bore 406 through the center of it.

The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 406 of the cylindrical magnet there is an imaging zone 408 where the magnetic field is strong and uniform enough to perform magnetic resonance imaging. The mechanical actuator 310 is shown as being in the bore of the magnet 406.

Within the bore 406 of the magnet there is also a set of magnetic field gradient coils 410 which are used for acquisition of magnetic resonance data to spatially encode magnetic spins within the imaging zone 408 of the magnet 404. The magnetic field gradient coils are connected to a magnetic field gradient coil power supply 412. The magnetic field gradient coils 410 are intended to be representative. Typically magnetic field gradient coils contain three separate sets of coils for spatially encoding in three orthogonal spatial directions. A magnetic field gradient power supply 412 supplies current to the magnetic field gradient coils 410. The current supplied to the magnetic field coils is controlled as a function of time and may be ramped or pulsed.

Adjacent to the imaging zone 408 is a radio-frequency coil 414 for manipulating the orientations of magnetic spins within the imaging zone 408 and for receiving radio transmissions from spins also within the imaging zone. The radio-frequency coil may contain multiple coil elements. The radio-frequency coil may also be referred to as a channel or an antenna. The radio-frequency coil 414 is connected to a radio frequency transceiver 416. The radio-frequency coil 414 and radio frequency transceiver 416 may be replaced by separate transmit and receive coils and a separate transmitter and receiver. It is understood that the radio-frequency coil 414 and the radio-frequency transceiver 416 are representative. The radio-frequency coil 414 is intended to also represent a dedicated transmit antenna and a dedicated receive antenna. Likewise the transceiver 416 may also represent a separate transmitter and receivers.

The mechanical actuator controller 312, the transceiver 416 and the magnetic field gradient coil power supply 412 are shown as being connected to the hardware interface 204 of the computer 202.

In this example the medial image data is magnetic resonance data. The computer storage 210 is further shown as containing a pulse sequence 420. The pulse sequence 420 is a set of commands or information which may be used to derive a set of commands for controlling the magnetic resonance imaging system 402 to acquire the magnetic resonance data 316. For instance the control module 224 could use the pulse sequence 420 to acquire the magnetic resonance data 316.

Figure 5:
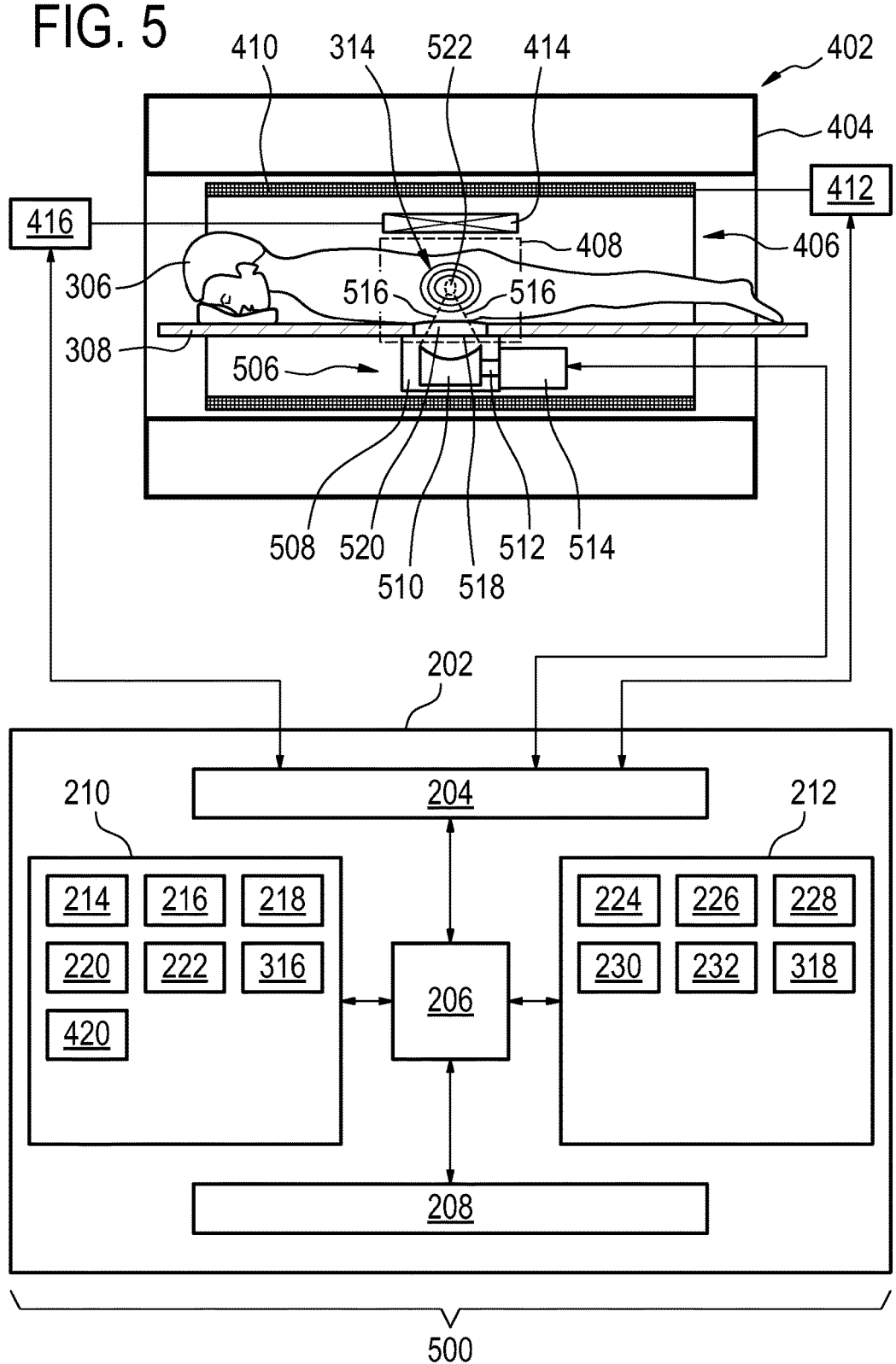
FIG. 5 illustrates a further example of a medical apparatus.

FIG. 5 shows a medical instrument 500 that is similar to the embodiment shown in FIG. 4. However, in FIG. 5 a high-intensity focused ultrasound system 506 is used instead of the mechanical actuator. The high-intensity focused ultrasound system 506 focuses the ultrasound to a point 522. By switching the ultrasound on or off or modulating it shear waves can be generated within the subject 306. The shear waves 314 can be shown as radiating outwards from the focal point 522.

A subject 306 is shown as reposing on a subject support 308. The medical apparatus 200 comprises a high-intensity focused ultrasound system 506. The high-intensity focused ultrasound system comprises 506 a fluid-filled chamber 508. Within the fluid-filled chamber 508 is an ultrasound transducer 510. Although it is not shown in this figure the ultrasound transducer 510 comprises multiple ultrasound transducer elements each capable of generating an individual beam of ultrasound. This may be used to steer the location of a focal point 522 electronically by controlling the phase and/or amplitude of alternating electrical current supplied to each of or groups of the ultrasound transducer elements. Point 522 represents the adjustable focus of the medical apparatus 500.

The ultrasound transducer 510 is connected to a mechanism 512 which allows the ultrasound transducer 510 to be repositioned mechanically. The mechanism 512 is connected to a mechanical actuator 514 which is adapted for actuating the mechanism 512. The mechanical actuator 512 also represents a power supply for supplying electrical power to the ultrasound transducer 510. In some embodiments the power supply may control the phase and/or amplitude of electrical power to individual ultrasound transducer elements.

The ultrasound transducer 510 generates ultrasound which is shown as following the path 516. The ultrasound 516 goes through the fluid-filled chamber 508 and through an ultrasound window 518. In this embodiment the ultrasound then passes through a gel pad 520. The gel pad 520 is not necessarily present in all embodiments but in this embodiment there is a recess in the subject support 308 for receiving a gel pad 520. The gel pad 520 helps couple ultrasonic power between the transducer 510 and the subject 306. After passing through the gel pad 520 the ultrasound 516 is focused to a sonication volume 522 or target zone.

The sonication volume 522 may be moved through a combination of mechanically positioning the ultrasonic transducer 510 and electronically steering the position of the sonication volume 522. By modulating or pulsing the intensity of ultrasound focused at the focal point 522 shear waves 314 can be induced in the subject.

Figure 6:
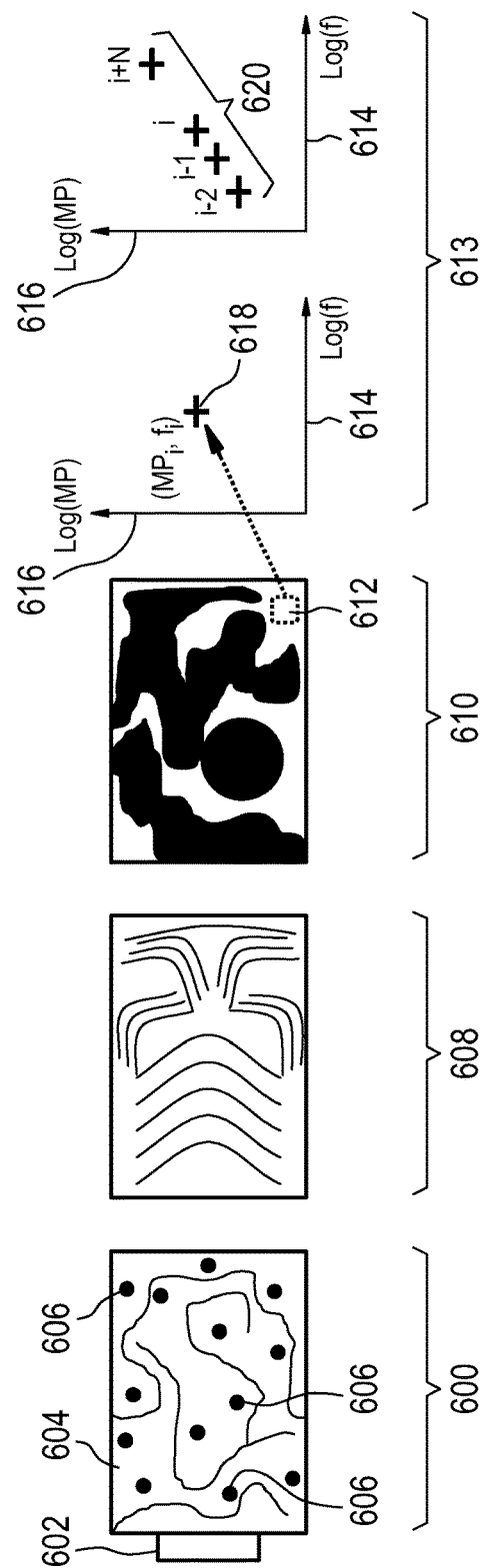
FIGS. 6 and 7 illustrate a series of images which are used to illustrate a portion of the method of determining the concentration distribution of the sonically dispersive elements.

FIG. 6 shows a series of images which are used to illustrate a portion of the method of determining the concentration distribution of the sonically dispersive elements. First image 600 shows a transducer for mechanical actuator 602 in contact with a matrix 604 filled with a variety of particulates 606. The ultrasound transducer 602 is able to induce a shear wave which is partially dispersed by the particulates 606. Next image 608 shows a shear wave image 608 or shear wave data that is descriptive of the transport of the shear wave through the matrix 604. A shear wave imaging system permits to acquire or register shear wave propagation.

Image 610 represents reconstructed images used for determining the mechanical properties. Dedicated software allows the reconstruction of mechanical properties from the theory of wave propagation. This may include but is not limited to the elasticity, viscosity, propagation, attenuation and the dispersion relation of the waves. Next image 613 shows two plots of the logarithm of the frequency 614 versus the logarithm of the mechanical property 616. A local volume 612 is indicated in the image 610. The local volume 612 is examined and the mechanical property at that particular point for this frequency is determined. This is plotted value 618 on the first plot. This is then repeated at multiple frequencies and the multiple plot values are shown as 620. The experiment is repeated at different frequencies in order to obtain a frequency dependence of the mechanical property.

Figure 7:
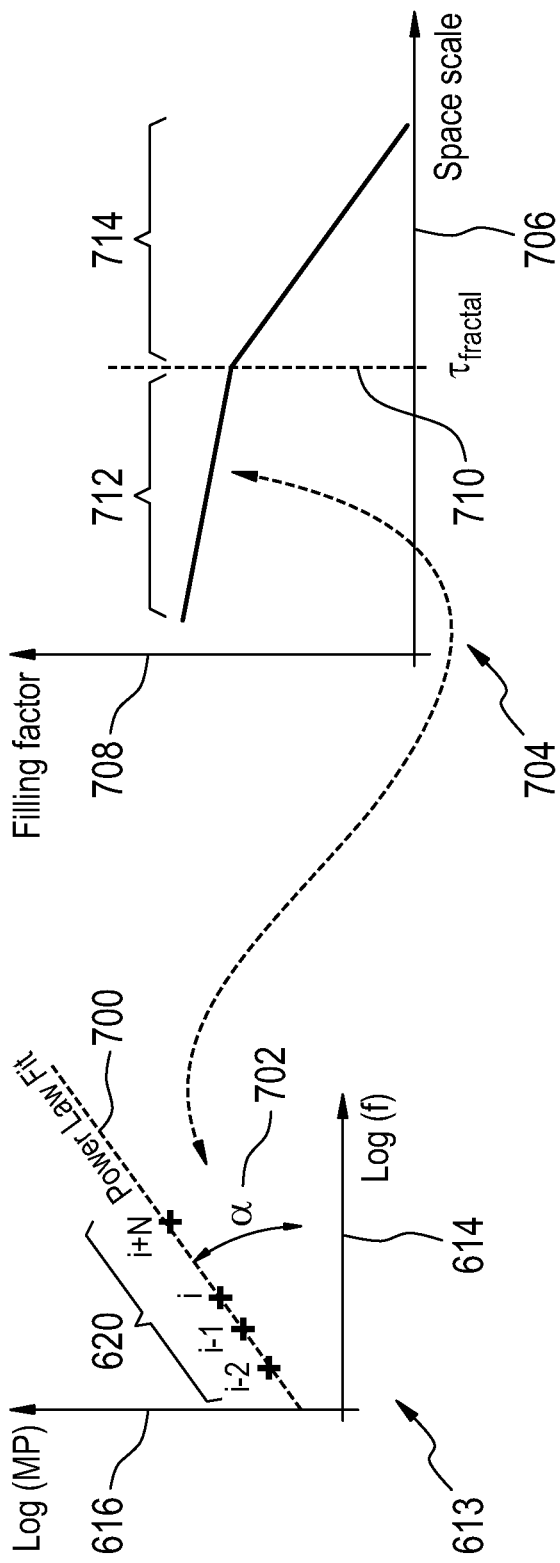

Next, FIG. 7 shows a portion of image 613 again. The multiple values 620 are plotted and a power law fit indicated by the dashed line is performed. The value of alpha is the slope of this line 702 and represents the power law fit. Extraction of the power law exponent alpha 702 characterizes the frequency dependence of the mechanical property. The image 704 illustrates one theoretical model which may be used for interpreting the particulate density in terms of alpha 702. This plot shows the spatial scale versus a filling factor calculated for a theoretical representation of particulates dispersed within a matrix. A box counting algorithm is used to characterize the volume or area being examined. On the spatial scale there is a value 710 which characterizes a transition between a normal fractal filling regime 712 and a normal Euclidian filling regime 714. The distribution of obstacles which may be for instance blood vessels or particles in space can be analyzed as a function of the spatial scale that is whether we look at the micrometer, the millimeter or the centimeter scale. It can be shown for example in image 704 that the filling space where obstacles changes between a classical geometrical filling and a fractal filling space for a given spatial scale 710. The anomalous part is linked to the exponent or the slope of alpha. This part is defined by the micro-architecture of the material, hence it is possible to deduce the details of the microarchitecture from the value of alpha 702, This is only feasible when the wavelength of the shear wave is sufficiently small to sense the fractal filling regime 712.

Figure 8:
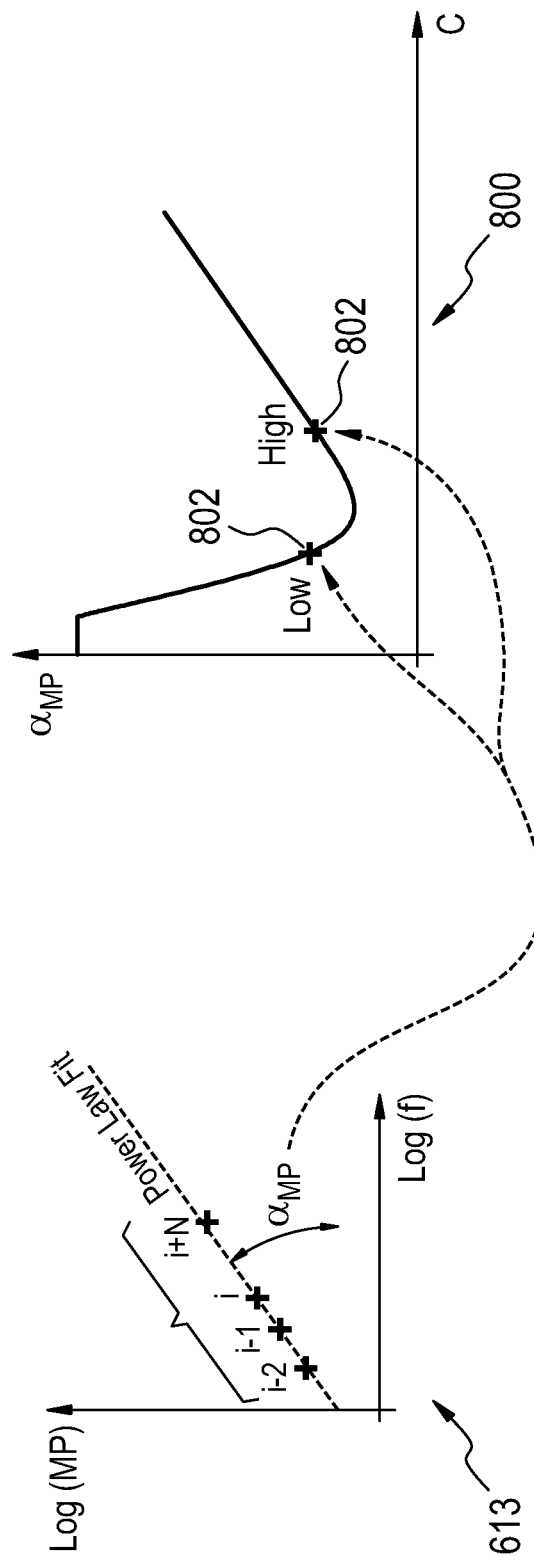
FIG. 8 illustrates multiple solutions to the calculation of the particulate concentration.

FIG. 8 illustrates that there may be multiple solutions to the particulate density. Image 613 is used to represent calculating alpha again. In plot 800 the concentration distribution versus the value of alpha is shown. There may be two solutions 802 for a particular measured value of alpha. This value was derived using theoretical derivation of the dispersion properties of the shear wave:

$$Disp = \tau_F^{df-d}\Gamma\left(df - d, \left(\frac{1}{\tau_F} \pm i\omega\right)t_0\right),$$

where Disp is measure if the measurement is within the fractal or Euclidian regime, df is the fractal dimension, d is the dimension, ω is the frequency being investigated, and $t_0$ is a characteristic time which is equivalent to the radius of the particulates. When Disp is much greater than one then there is a fractal effect, and when Disp is much less than one there no fractal effect. A brief outline of the theory of this above equation is contained in the following appendix. In particular see the portion of Eq. 9 labeled "general weight" in the appendix.

For a given measurement the concentration or the distribution of concentration may have more than one solution. To get the concentration from the experimental data the use of a knowledge of the macroscopic pathology may be used to determine the radius and a priori information may be used to distinguish between the two possible solutions. For instance it may be known what sort of blood vessels or particulates are inside of the subject. This would allow elimination of one of the possible solutions.

Figure 9:
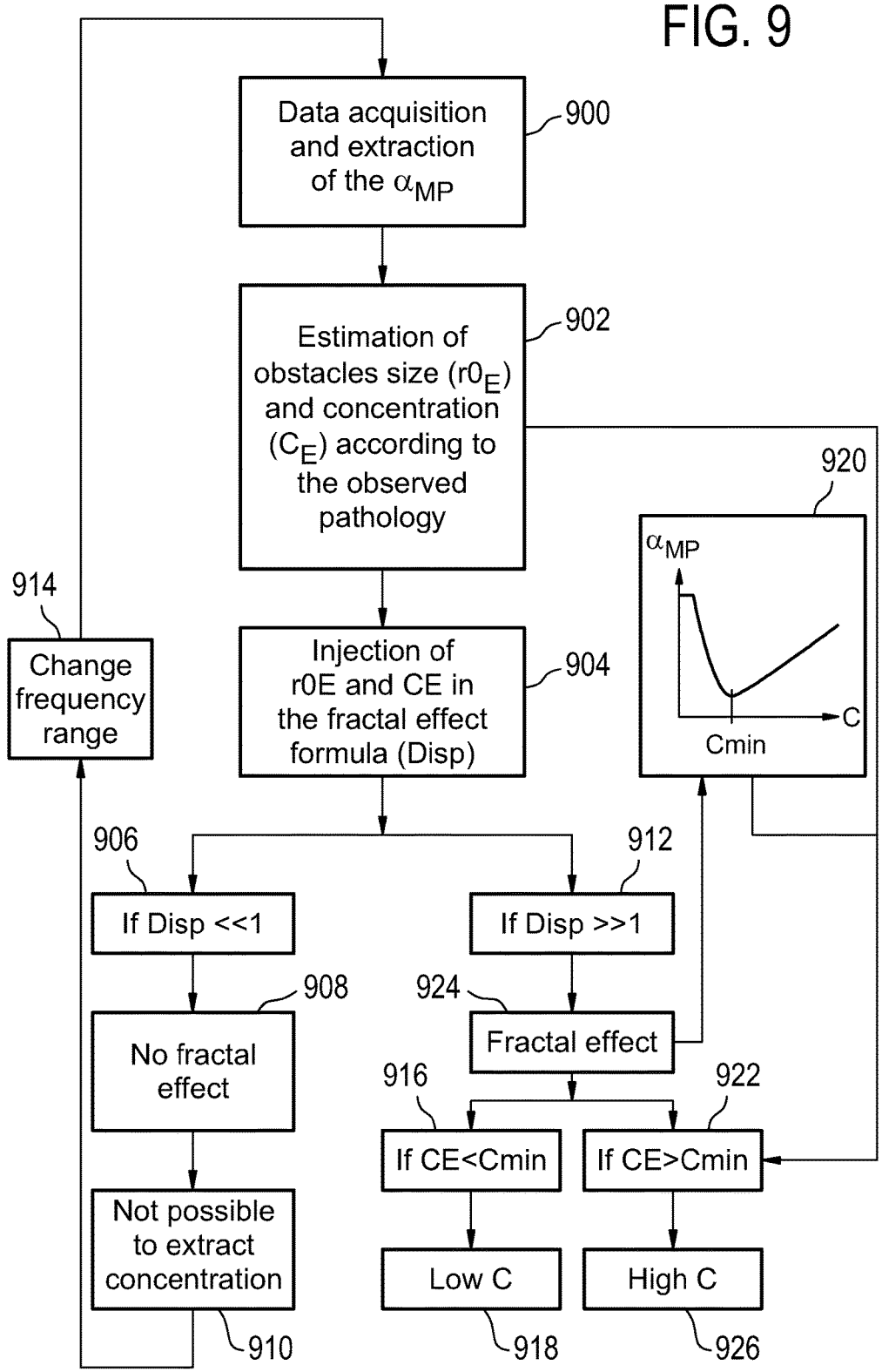
FIG. 9 shows a flow diagram which illustrates how the correct solution can be determined.

FIG. 9 shows a method of determining the correct solution. In step 900 data acquisition and extraction of the value of $\alpha_{mp}$ is determined, wherein $\alpha_{mp}$ is the power law relationship for the mechanical property mp. Next in step 902 an estimation of the obstacle size and concentration or concentration distribution according to an observed pathology is determined. Next in step 904 the injection of $rO_E$, the size range of the particulates, and $C_E$, the concentration range, in the fractal effect formula (Disp, shown above) is performed. Choosing $rO_E$ and $C_E$ imparts some $_a$ priori knowledge of the microstructure and enables determining the solution.

If the value of Disp is much less than 1 then branch 906 is selected. In this case there is no fractal effect 908 and it is not possible to extract the concentration 910. In this case the frequency is changed 914 and the method returns to step 900. In case the value Disp is much greater than 1 912 then there is a fractal effect 924. If $C_E$ is much less than $C_{min}$ (the lower minimum concentration solution) then the low concentration 918 is selected. If the concentration is at the minimum 920 then there is only one solution and the solution is known. If $C_E$ is greater than $C_{min}$ then the high concentration is selected 926. The use of equation Disp is not necessary. Experiments or numerical simulations could be performed to determine the relation between $\alpha_{mp}$ and the concentration.

Magnetic Resonance Elastography (MRE) is a technique capable of noninvasively assessing the mechanical properties of tissues. The assessment of these properties is done indirectly via the measurement of low frequency mechanical shear waves traversing the tissue. It can be hypothesized that the presence of micro-obstacles—similar to effects leading to the apparent diffusion coefficient—changes the dispersion relation of propagating shear waves and hence might influence at the macroscopic scale the apparent mechanical properties of the medium. In diffusion weighted imaging (DWI), disordered media can lead to two effects: reduction of the typical diffusion length leading to the apparent diffusion coefficient and/or a mean-square displacement which is not anymore proportional to time but to a fractional power of time not equal to one (so-called anomalous diffusion). In DWI, micro-structural information is lost due to the massive averaging that occurs within the imaging voxel and can only be revealed when exploring the tissue using different b-values. Similarly here, where the propagation of a mechanical wave enters into the diffusive regime due to multiple scattering effects, the frequency dependence of the mechanical properties could allow the assessment of the sub-voxel microarchitecture. In this study we investigate the propagation of shear waves in calibrated phantoms containing accurately controlled size distributions of scattering particles and demonstrate for the first time that shear waves are able to reveal at the macroscopic scale the hidden microarchitecture properties of the material.

To test this experimental, gel phantoms were fabricated using an agarose solution at 15 g/L (BRL, Type 5510UB) prepared in a water bath at 80° C. In order to create well defined scattering particle size distributions, colloidal suspensions of polystyrene microspheres with precisely known diameter (1 μm, 5 μm, 10 μm, 30 μm and 150 μm diameter, Sigma-Aldrich) and concentrations were added to the gel before solidification. This is shown in FIG. 10.

Figure 10:
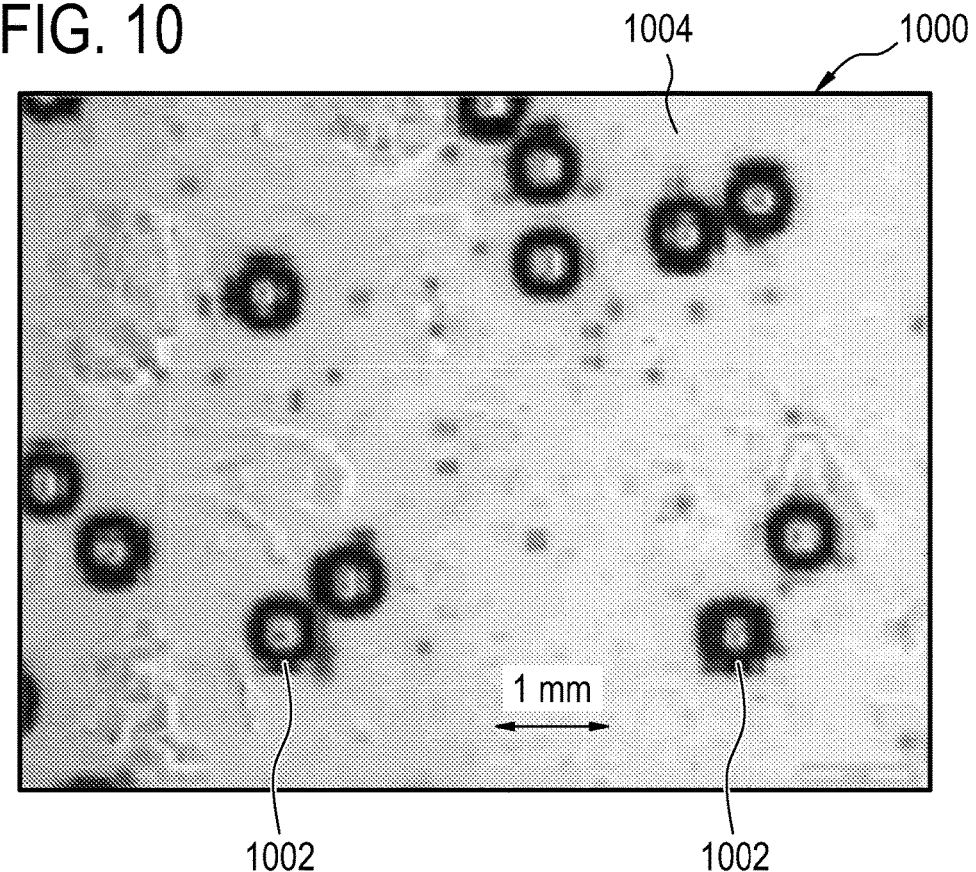
FIG. 10 shows a light microscopy image of a colloidal gel specimen with particulates embedded.

FIG. 10 shows a light microscopy image 1000 of a colloidal gel specimen 1004 with particulates embedded 1002. The image was taken at a magnification of 50× using a Leica microscope. Clearly, particles of different sizes can be identified. The thereby measured diameter distribution per volume corresponds to the expected theoretical value hence validating the desired microarchitectural properties of the gel.

The aim was to maintain for all prepared gels a concentration of 8% of spheres (similar to the volume fraction of blood vessels in tissue). The polystyrene microspheres have an extremely elevated shear modulus (~MPa) and hence can serve as microscopic scatterers in the soft gel (~kPa). Different sample were prepared: gels without spheres serving as reference, gels with only one type of spheres (so-called monosize gel) and gels with particle size distributions which followed a power law and hence possessed fractal properties. Different exponents of power-law particle size distributions (#~$d^{\gamma}$, with d the particle diameter) were fabricated ($\gamma$ =−2, −1, 0). A $\gamma$-value of zero indicates a flat distribution meaning that as many small as large particles are present. MRE was performed on a horizontal 7 T imaging scanner (Pharmascan, Bruker, Erlangen, Germany). Mechanical vibrations were generated by a toothpick placed in the center of the sample to induce a circular propagation. An electromagnetic shaker located outside the MR scanner was used to transmit mechanical vibrations via a flexible carbon fiber rod to the toothpick. This is shown in FIG. 11.

Figure 11:
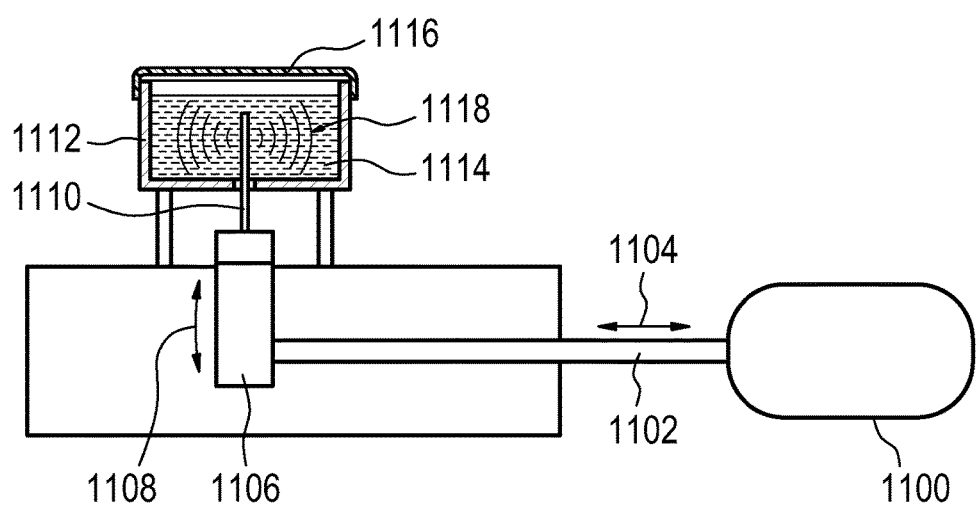
FIG. 11 illustrates an experimental setup.

FIG. 11 shows a schematic description of the experimental setup used. The gel is filled into an insert which is mounted onto the MRE setup. FIG. 11 shows an example of the experimental setup. There is a electromagnetic shaker 1100 which is connected to a carbon rod 1102. The electromagnetic shaker 1100 causes the carbon rod 1102 to move in the direction indicated by the arrows 1104. The carbon rod 1102 is connected to a cradle 1106. The cradle 1106 translates the motion of the rod 1104 into a different motion indicated by the arrows 1108. 1108 is transverse to 1104. A toothpick 1110 is mounted in the cradle 1106. The toothpick 1110 is inserted into a container 1112 that is filled with a gel 1114 and sealed with parafilm 1116. The toothpick 1110 vibrates up and down inducing shear waves 1118 in the gel 1114.

Samples placed around the toothpick 1110 were always at the same height via a home-made support. A surface receiver coil was placed around the sample at the level of the gel to assure optimal signal-to-noise. For each phantom a steady-state MRE sequence was applied with a mechanical excitation frequency in the range of 150 to 300 Hz and the following sequence parameter: 8 dynamics, 7 contiguous transverse slices with slice thickness of 0.4 mm, field of view=25 mm×25 mm, matrix size=256×256, TE/TR=27–17/427–353 ms and acquisition time in the range of 6 to 10 min depending on the excitation frequency and on the number of motion encoding gradient periods. The MRE sequence was acquired for the three spatial direction of motion in order to obtain volumetric images of the 3D propagating mechanical wave inside the phantom. In order to take into account a potential temporal evolution of the gel during the entire acquisition time (up to 300 mins!), the first experiment was repeated at the end of the acquisition time. This allowed correcting for potentially drying effect. Data was reconstructed with an isotropic reconstruction technique.

In examining the experimental results, the complex-shear modulus (G*) of each phantom increased by a maximum of 10% between the beginning and the end of the multifrequency-MRE experiment due to aging effects. As presented in FIG. 2, results show that the macroscopic shear modulus is frequency-dependant for the four investigated samples and follows a power law with $|G^*(\omega)|=\alpha \cdot \omega^{z_0}$. The power coefficient $z_0$ of a gel with the 10 μm-monosize distribution of microspheres is almost unchanged as compared to $z_0$ of the reference gel, shown in FIGS. 12 and 13.

Figure 12:
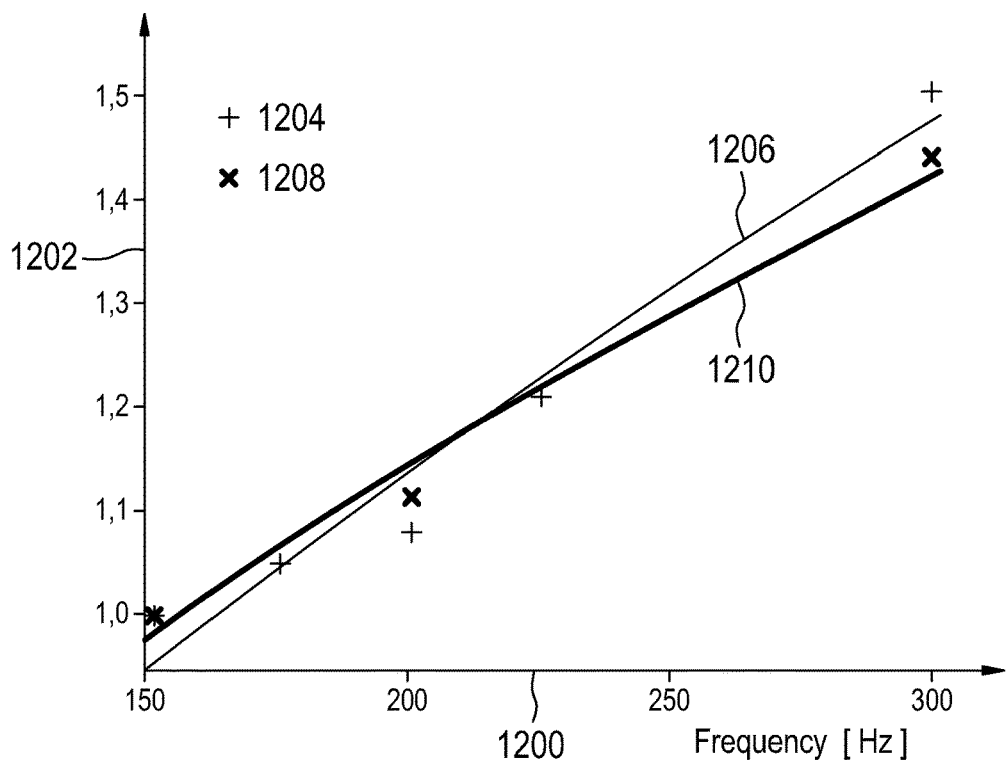
FIG. 12 shows a plot of experimental data.

FIG. 12 shows a plot of experimental data. FIG. 12 is a plot of the frequency in Hertz 1200 versus the normalized complex shear modulus 1202. The + marked points 1204 are measurements for gel with 10 μm. The line 1206 is a power law fit to the data 1204. The points marked with an x 1208 are taken for the reference gel. The line 1210 is a power law fit to 1208.

Figure 13:
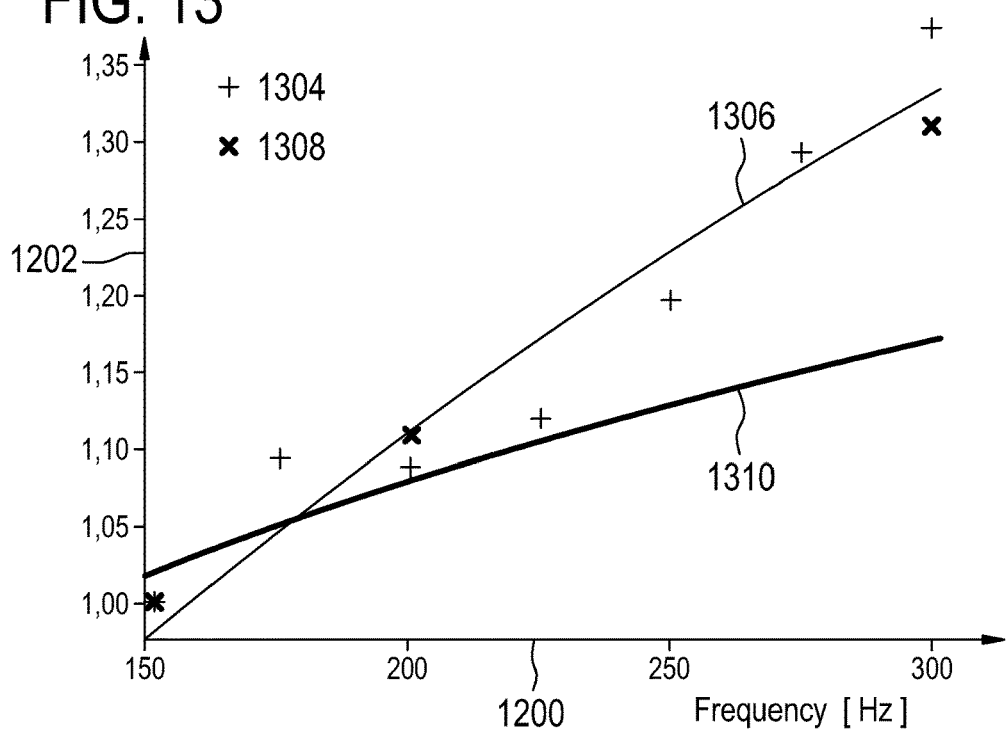
FIG. 13 shows a further plot of experimental data.

FIG. 13 shows more experimental data. The points labeled 1304 or a + correspond to a fractal of a gamma=0. The line 1306 is a power law fit to the data 1304. The data marked with an x 1308 is the reference gel. The line 1310 is a power law fit to the data 1308.

However, in the presence of a fractal distribution of microspheres, $z_0$ increases significantly compared to the reference gel by a factor of 2.2. All other fractal gels demonstrated equally a significant increase in $z_0$.

The experimental tests demonstrate that the frequency-dependence of mechanical shear wave diffusion can allow probing sub-voxel distributions of scattering structures and as a consequence overcome the spatial resolution limitation relying intrinsically on the MR imaging sensitivity. These experimental results have been theoretically and numerically via FEM simulations confirmed (not shown). However, in this study mechanical properties of the gel were critically relying on the fabrication process and only relative slopes of different gels have been compared. The solidification process of the colloidal gels must be improved and additional imaging modalities should be involved such as CT-scans in order to image the microspheres distribution in phantoms after solidification of the gel that probably induces microspheres aggregation into fractal flocs. Moreover, the studied gels consisted of very simplified biphasic structural arrangements with particles being about 1000 times stiffer than the background gel. Biological tissue represents a far more complex arrangement with variations not only in size, but also in stiffness contrast and length distribution. Phantoms with microspheres exhibiting multi-size distributions and multiple elasticity properties would be better to simulate real tissue. The here observed effect might play an important role in understanding the influence of microscopic tissue components on mechanical properties as measured by elastography techniques. It opens the perspective of detecting and describing micro-inclusions, such as small metastases or neo-vascularisation, from elastography data, which are not directly detectable by MRE.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

APPENDIX

Figure 14:
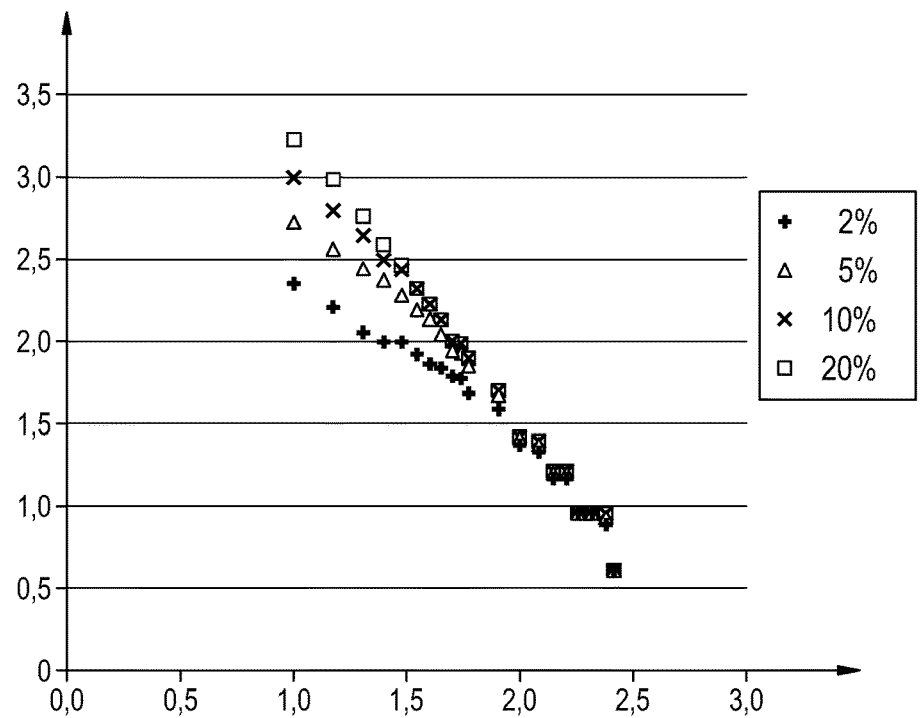
FIG. 14 shows Box-counting results for different densities of a fixed particle size.

Geometrical Characterization of the Material Via Box-Counting: Pair-Correlation Function We will investigate how to characterize a simple homogeneous elastic medium (no viscosity) which is filled with very stiff particles of a fixed size. For that purpose we will use the box-counting method as shown in FIG. 14. FIG. 14 shows Box-counting results for different densities and a fixed particle diameter of 10 μm.

This diameter corresponds to 1=log(10) on the x-axis.

We can identify two distinct regions for this type of composite material which separate at the characteristic length $\zeta$ such that $$N(r) \sim r^{df} < \zeta \quad (1)$$

$$N(r) \sim r^{D} < \zeta \quad (2)$$

where we have introduced df as fractal dimension. This can be considered here as its definition and as such df represents the power-law exponent within a certain bandwidth.

Figure 15:
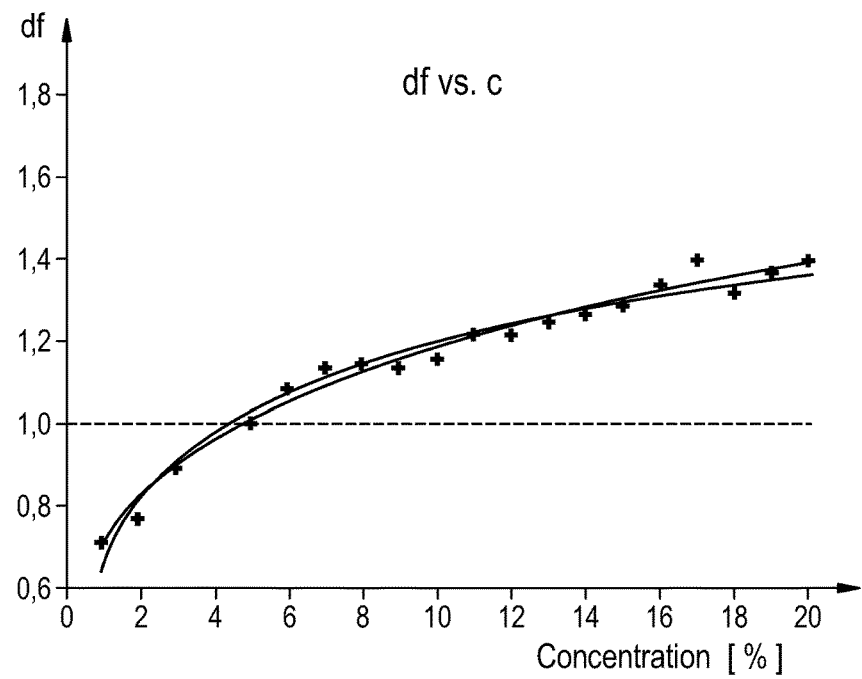
FIG. 15 shows an example of the fractal dimension df as a function of concentration.

For low densities we observe df≈1 while for higher densities df approaches 2 for those 2D simulations (see FIG. 15). FIG. 15 shows the fractal dimension df (i.e. slope of non-euclidean part in FIG. 14) as a function of concentration.

Figure 16:
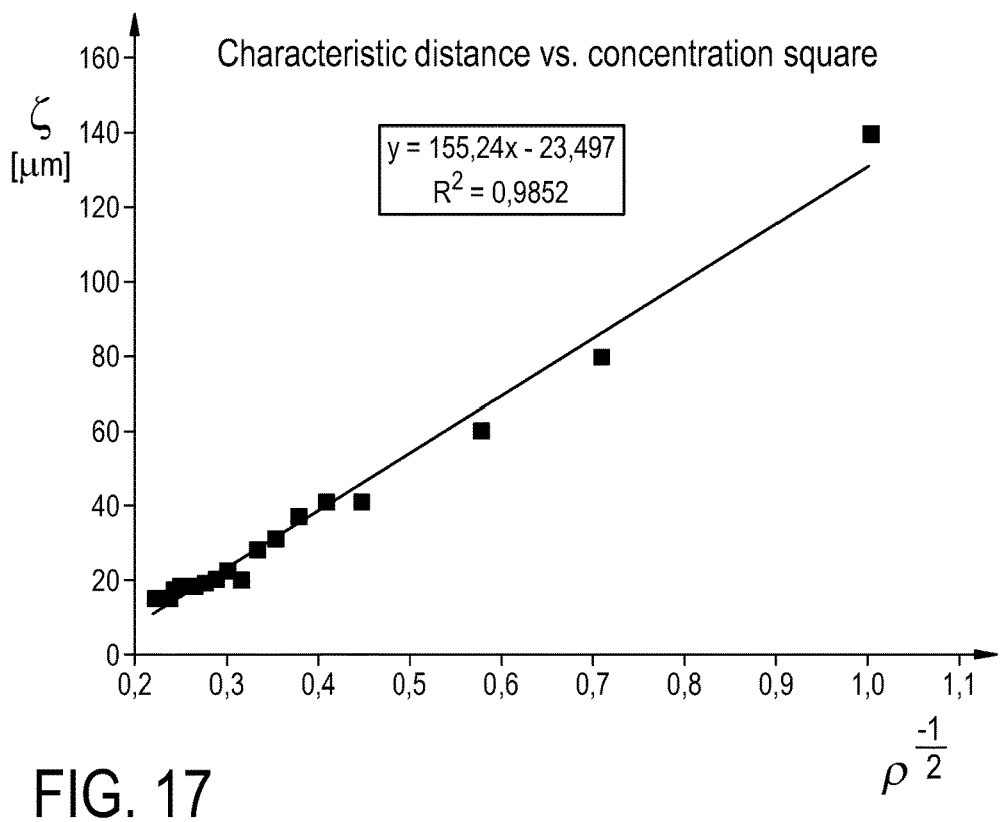
FIG. 16 shows the characteristic length ζ (in units of pixels=μm here) as a function of $$\rho^{-\frac{1}{D}}$$

This dependence is not derived from first principles. It is merely an experimental result. However, since the material does not form any complex aggregates, the characteristic length $\zeta$ must follow under these conditions the simple geometric relationship $$\zeta \propto \rho^{-\frac{1}{D}} \quad (3)$$

with ρ the density of particles submersed in the homogeneous background. This relationship is shown in FIG. 16.

In order to evaluate the probability of finding at distance r a particle (i.e. we are searching the so-called pair-correlation function), we follow the approach of Teixeira, see Teixeira, J. Small-angle scattering by fractal systems. J. Appl. Cryst 21, 781-785 (1988). The number of particles within the radius r from the origin can be written as $$N(r) = \int_0^r dr P(r) \cdot \pi (2r)^{D-1}. \quad (4)$$

Differentiation of Eqs. 2 and 4 leads to the following expression for the probability density function:

$$P(r) \sim r^{df-D} \quad (5)$$

Apparently, in case of an euclidean distribution with df≡D, we find $P(r) \sim r^0$ which leads to $N(r) \sim r$ as expected. If we consider the background of the material as constant and isotropic, this probability density represents the lag-time distribution for a material since it describes how likely it is to find at distance r another obstacle. That is the key idea in order to connect this fractal part with the ODA theory. FIG. 16 shows the characteristic length $\zeta$ (in units of pixels=μm here) as a function of $$\rho^{-\frac{1}{D}}$$

with D=2 here.

The results of FIGS. 14 to 16 hence provide the following parameterizations $$df \approx \frac{1}{15}(p-5)+1 \quad (6)$$

$$\zeta \approx 155[\mu m] \cdot \rho^{-1/2} \quad (7)$$

with the concentration ρ in %.

With this knowledge we can now construct a lag-time distribution which allows to analytically solve the necessary equations in ODA to calculate the dispersion properties of the propagation β. Hence, the lag-time distribution a(t) is composed of two terms: one term describing the fractal part and one the classical euclidean part. The limit of validity of the fractal part is given by the characteristic length $\zeta$ which is called in the temporal domain $\tau_F = \zeta/c_0$ with $c_0$ the speed of the wave in the background material. In order to render the equations analytical we use exponential functions for the suppression. The Euclidean part is accordingly suppressed for small distances by $1-e^{-t/\tau_F}$. In order to prevent lag-times of infinite value, the euclidean part is furthermore suppressed by an exponential function with the characteristic time constant $\tau_D$ with $\tau_F < \tau_D$. This yields the following lag-time distribution (see FIG. 17):

$$a(t) = t^{df-D-1} e^{-t/\tau_F} + t^{-1}(1-e^{-t/\tau_F}) e^{-t/\tau_D}, \quad (8)$$

where an addition 1/r has been introduced since we want to use the probability density as developed for the dimensionality D for the ODA theory which operates in 1D!

FIG. 17 shows the schematic depiction of the two contributions for the total lag-time distribution a(t). The finite particle size limits the analysis to $t > t_0 = r_0/c_0$.

The translation from lag-time distribution to dispersion relation for β necessitates to calculate the Fourier sinus transform of a(l), i.e. we need to calculate the characteristic equation (see Gradshteyn, I. S. & Ryzhik, I. M. Table of Integrals, Series, and Products (Academic Press, Burlington, Mass., 2007), 7th edn. p.498/eq.2):

$$2. \int_u^\infty x^{\mu-1} e^{-\beta x} \sin \delta x \, dx = \quad \text{ET | 318(9)}$$

$$\frac{i}{2}(\beta+i\delta)^{-\mu} \Gamma[\mu,(\beta+i\delta)u] - \frac{i}{2}(\beta-i\delta)^{-\mu} \Gamma[\mu,(\beta-i\delta)u]$$

$$[\text{Re}\beta > |\text{Im}\delta|]$$

$$\int_{t_0}^\infty dt\, t^{(df-D)-1} e^{-t/\tau_F} \sin(\omega t) = \quad (9)$$

$$\frac{i}{2}\left(\frac{1}{\tau_F}+i\omega\right)^{D-df} \Gamma\left(df-D,\left(\frac{1}{\tau_F}+i\omega\right)t_0\right) -$$

$$\frac{i}{2}\left(\frac{1}{\tau_F}-i\omega\right)^{D-df} \Gamma\left(df-D,\left(\frac{1}{\tau_F}-i\omega\right)t_0\right) =$$

$$\tau_F^{(df-D)} \Gamma\left(df-D,\left(\frac{1}{\tau_F}+i\omega\right)t_0\right) \cdot$$

$$\frac{i}{2}[(1+i\omega\tau_F)^{D-df} - (1-i\omega\tau_F)^{D-df}] =$$

$$\underbrace{(-)\tau_F^{(df-D)} \Gamma\left(df-D,\left(\frac{1}{\tau_F}+i\omega\right)t_0\right) \cdot (1+(\omega\tau_F)^2)^{\frac{D-df}{2}}}_{\text{general weight}}$$

$$\sin((D-df)\mathrm{atan}(\omega\tau_F))$$

Apparently, for df→D the Fourier sinus integral yields zero. Thus, the multiple reflections from the Euclidean part of the distribution do not contribute to β. The different terms of Eq. 8 yield hence the following expression for the propagation of the wave:

$$\beta(\omega) = \underbrace{\alpha\omega}_{direct\ beam} + \underbrace{(1+(\omega\tau_F)^2)^{\frac{D-df}{2}}\sin((D-df)\operatorname{atan}(\omega\tau_F))}_{reflected\ beam}, \quad (10)$$

with $\alpha$ a scale factor for the direct beam (which is of the order of $\tau_F$) and $$\tau = (\tau_D * \tau_F)/(\tau_D + \tau_F) \quad (11)$$

$$\tau_F = N \times t_0 = \frac{155\ [\mu m]}{c_0} \cdot \rho^{-\frac{1}{2}} \quad (12)$$

$$\tau_D = M \times t_0 > \tau_F \quad (13)$$

$$df = \frac{1}{15}(\rho - 5) + 1 \quad (14)$$

LIST OF REFERENCE NUMERALS 200 medical apparatus
202 computer
204 hardware interface
206 processor
208 user interface
210 computer storage
212 computer memory
214 shear wave data
216 mechanical property
218 power law relationship
220 concentration distribution of sonically dispersive elements
222 calibration data
224 control module
226 shear wave data processing module
228 power law determination module
230 concentration determination module
232 calibration data generation module
300 medical apparatus
302 medical imaging system
304 imaging zone
306 subject
308 subject support
310 mechanical actuator
312 mechanical actuator controller
314 shear waves
316 medical image data
318 image processing module
400 medical apparatus
402 magnetic resonance imaging system
404 magnet
406 bore of magnet
408 imaging zone
410 magnetic field gradient coils
412 magnetic field gradient coils power supply
414 radio-frequency coil
416 transceiver
420 pulse sequence
500 medical apparatus
506 high intensity focused ultrasound system
508 fluid filled chamber
510 ultrasound transducer
512 mechanism
514 mechanical actuator/power supply
516 path of ultrasound
518 ultrasound window
520 gel pad
522 focal point
600 excitation step
602 ultrasound transducer
604 matrix
606 particulate
608 shear wave imaging
610 reconstructed images
612 local value
613 plot of mechanical parameter vs. frequency
614 log of frequency
616 log of mechanical property
618 value
620 multiple values
700 power law fit
702 alpha
704 plot
706 spatial scale
708 filling factor
710 concentration inflection
712 abnormal fractal filling
714 normal Euclidean filling
800 plot
802 two solutions
1000 image
1002 particulates
1004 gel
1100 electromagnetic shaker
1102 carbon rod
1104 mechanical motion of rod
1106 cradle
1108 motion of cradle
1110 toothpick
1112 container
1114 gel
1116 cover
1118 shear waves
1200 frequency Hz
1202 Normalized complex shear modulus
1204 gel with 10 μm microspheres
1206 power law fit to 1204
1208 reference gel
1210 power law fit to 1208
1304 fractal with gamma=0
1306 power law fit to 1304
1308 reference gel
1310 power law fit to 1308

The invention claimed is:

1. A medical apparatus for determining a concentration distribution of sonically dispersive elements within a subject, the medical apparatus comprising:
   a medical imaging system;
   a vibration system;
   a memory for storing machine executable instructions;
   a processor for executing the machine executable instructions, wherein execution of the instructions cause the processor to:
   control the vibration system to cause shear waves in the subject;
   control the medical imaging system to acquire shear wave data using the medical imaging system, wherein the shear wave data is descriptive of a propagation of the shear waves within the subject for at least two frequencies;
   determine a mechanical property of the subject using the shear wave data;

determine a power law relationship between the at least two frequencies and the mechanical property;

determine calibration data by modeling scattering of shear waves by the sonically dispersive elements as a function of the shear wave frequency;

determine the concentration distribution of the sonically dispersive elements within the subject using the power law relationship and the calibration data;

and displaying the concentration distribution of the sonically dispersive elements on a display, wherein the sonically dispersive elements are blood vessels within the subject, and execution of the instructions cause the processor to determine the concentration distribution of the blood vessels within the subject using the power law relationship and the calibration data wherein the calibration data comprises an average size of blood vessels within the subject.

2. The medical apparatus of claim 1, wherein the medical imaging system is an ultrasound system,
wherein the ultrasound system is arranged to acquire ultrasound data,
wherein the ultrasound system is arranged to determine the shear wave data by tracking speckle patterns in the ultrasound data.

3. The medical apparatus of claim 1, wherein the medical imaging system is a magnetic resonance imaging system,
wherein the magnetic resonance imaging system is arranged to acquire magnetic resonance elastography data,
wherein the magnetic resonance imaging system is arranged to determine the shear wave data using the magnetic resonance elastography data.

4. The medical apparatus of claim 1, wherein the vibration system comprises one of an ultrasound transducer or a mechanical actuator.

5. The medical apparatus of claim 1, wherein the vibration system comprises a high intensity focused ultrasound system,
wherein the high intensity focused ultrasound system is operable for inducing the shear waves using sonic radiation force.

6. The medical apparatus of claim 1, wherein the vibration system is operable to generate shear waves with a frequency of 10 Hz to 1000 Hz.

7. The medical apparatus of claim 1, wherein the shear wave data, the mechanical property, the power law relationship, and the concentration distribution of the sonically dispersive elements have a two-dimensional spatial dependence.

8. The medical apparatus of claim 1, wherein execution of the machine executable instructions further cause the processor to perform an operation selected from the group consisting of storing the concentration distribution of the sonically dispersive elements in the memory, sending the concentration distribution of the sonically dispersive elements to a computer system via a computer network, and combinations thereof.

9. The medical apparatus of claim 1, wherein execution of the machine executable instructions further cause the processor to generate the calibration data by modeling the scattering of shear waves by the sonically dispersive elements as a function of shear wave frequency and sonically dispersive element size.

10. The medical apparatus of claim 1, wherein the mechanical property selected from the group consisting of elasticity, viscosity, propagation, attenuation, and the dispersion relation.

11. The medical apparatus of claim 1, wherein the shear wave data, the mechanical property, the power law relationship, and the concentration distribution of the sonically dispersive elements have a three-dimensional spatial dependence.

12. A non-transitory computer readable medium comprising machine executable instructions for execution by a processor controlling a medical apparatus, the medical apparatus arranged to determine a density distribution of blood vessels within a subject, wherein execution of the instructions cause the processor to:
receive shear wave data, wherein the shear wave data describes a propagation of shear waves within the subject for at least two frequencies;
determine a mechanical property of the subject using the shear wave data at each of the at least two frequencies;
determine a power law relationship between the at least two frequencies and the mechanical property; and
determine the density distribution of blood vessels within the subject using the power law relationship and calibration data comprising an average or typical size of blood vessels within the subject;
wherein the density distribution of blood vessels within the subject is used to determine information of the blood vessels to diagnosis the patient with a pathology.

13. The non-transitory computer readable medium of claim 12, wherein the shear wave data, the mechanical property, the power law relationship, and the density distribution of blood vessels in within the subject have a three-dimensional spatial dependence.

14. The non-transitory computer readable medium of claim 12, wherein execution of the machine executable instructions further cause the processor to perform at least one operation selected from the group consisting of:
storing the density distribution of blood vessels within the subject in a memory,
displaying the density distribution of blood vessels within the subject on a display, and
sending the density distribution of blood vessels within the subject to a computer system via a computer network.

15. A medical apparatus for determining a density distribution of blood vessels within a subject, the medical apparatus comprising:
a medical imaging system;
a vibration system;
and the non-transitory computer readable medium of claim 12, wherein execution of the instructions further cause the processor to:
control the vibration system to cause the shear waves within the subject using the vibration system; and
control the medical imaging system to acquire the shear wave data.

16. A method of determining the concentration distribution of sonically dispersive elements within a subject, wherein the method comprises the steps of:
receiving shear wave data, wherein the shear wave data describes the propagation of shear waves within the subject for at least two frequencies;
determining a mechanical property of the subject using the shear wave data at each of the at least two frequencies, the mechanical property including one of elasticity, propagation, and the dispersion relation;
determining a power law relationship between the at least two frequencies and the mechanical property; and determining the concentration distribution of the sonically dispersive elements within the subject using the power law relationship and calibration data;

wherein the concentration distribution of the sonically dispersive elements within the subject is used to determine information of the sonically dispersive elements to diagnosis the patient with a pathology; and wherein the sonically dispersive elements are blood vessels within the subject, and determining the concentration distribution of the blood vessels within the subject using the power law relationship and the calibration data wherein the calibration data comprises an average size of blood vessels within the subject.

17. The method of claim 16, wherein the method further comprises the steps of:

measuring a calibration power law relationship as a function of the concentration distribution of dispersive elements; and determining the calibration data empirically using the calibration power law relationship.

18. The method of claim 16, wherein the shear wave data, the mechanical property, the power law relationship, and the concentration distribution of the sonically dispersive elements have a three-dimensional spatial dependence.

19. The method of claim 16, further including at least one of:

storing the concentration distribution of the sonically dispersive elements in a memory, displaying the concentration distribution of the sonically dispersive elements on a display, and sending the concentration distribution of the sonically dispersive elements to a computer system via a computer network.

* * * * *